(12) United States Patent
Wiest et al.

(10) Patent No.: US 11,077,247 B2
(45) Date of Patent: *Aug. 3, 2021

(54) INTRAVENOUS TUBING SET MODIFIED FOR IN-LINE CATHETER FLUSHING

(71) Applicant: Becton, Dickinson and Company, Franklin Lakes, NJ (US)

(72) Inventors: Kathleen Wiest, Naperville, IL (US); Lindsay Miller, Charlotte, NC (US); Jessica Williams, Amarillo, TX (US); Rebecca Zaunbrecher, Concord, MA (US); Ann Saterbak, Houston, TX (US); Z. Maria Oden, Houston, TX (US); Andrew Geiszler, Great Falls, MT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 173 days.

This patent is subject to a terminal disclaimer.

(21) Appl. No.: 16/379,963

(22) Filed: Apr. 10, 2019

(65) Prior Publication Data

US 2019/0231976 A1     Aug. 1, 2019

Related U.S. Application Data

(63) Continuation of application No. 14/230,413, filed on Mar. 31, 2014, now Pat. No. 10,293,106.

(Continued)

(51) Int. Cl.
*A61M 5/168*     (2006.01)
*A61M 5/14*     (2006.01)

(52) U.S. Cl.
CPC .......... *A61M 5/16827* (2013.01); *A61M 5/14* (2013.01); *A61M 5/1409* (2013.01);

(Continued)

(58) Field of Classification Search
CPC .. A61M 5/16827; A61M 5/14; A61M 5/1409; A61M 2005/1403
See application file for complete search history.

(56) References Cited

U.S. PATENT DOCUMENTS 3,844,283 A     10/1974 Dabney
4,119,267 A *   10/1978 Kydonieus ................ A61J 1/10
                                                          604/408

(Continued)

FOREIGN PATENT DOCUMENTS

GB       1481427       7/1977
JP       S50044689     10/1974

(Continued)

OTHER PUBLICATIONS

"PCT International Search Report and Written Opinion in PCT/US2014/032506", dated Jul. 31, 2014, 10 pages.

*Primary Examiner* — Bradley J Osinski
(74) *Attorney, Agent, or Firm* — Servilla Whitney LLC

(57) ABSTRACT

An intravenous tubing set is provided having a coupling component for accessing a source of flush solution; a flush chamber; a first IV tubing for delivering saline solution from the source of flush solution to the flush chamber; a first flow control device disposed in the tubing between the source of flush solution and the flush chamber to control the flow of flush solution into the flush chamber; a second IV tubing for delivering flush solution to a patient catheter; and a second flow control device disposed in the second tubing between the flush chamber and the patient catheter.

17 Claims, 5 Drawing Sheets

Related U.S. Application Data

(60) Provisional application No. 61/807,941, filed on Apr. 3, 2013.

(52) U.S. Cl.
CPC ............... *A61M 2005/1403* (2013.01); *A61M 2205/582* (2013.01)

(56) References Cited

U.S. PATENT DOCUMENTS

| | | |
|---|---|---|
| 4,236,515 A | 12/1980 | Genese |
| 4,563,173 A | 1/1986 | Ledley |
| 4,641,362 A * | 2/1987 | Muller ..................... A61J 1/10 383/113 |
| 4,692,144 A | 9/1987 | Carpenter |
| 5,242,392 A * | 9/1993 | Vaughn ............... A61M 5/1408 604/80 |
| 5,330,447 A | 7/1994 | Barth |
| 5,779,678 A * | 7/1998 | Carter ................. A61M 5/1424 604/140 |
| 5,863,436 A | 1/1999 | Matkovich |
| 2009/0306621 A1 | 12/2009 | Thome, Jr. et al. |
| 2011/0020322 A1 | 8/2011 | Chen et al. |

FOREIGN PATENT DOCUMENTS

| | | |
|---|---|---|
| JP | H1028720 A | 2/1998 |
| JP | 2006141827 A | 6/2006 |

\* cited by examiner

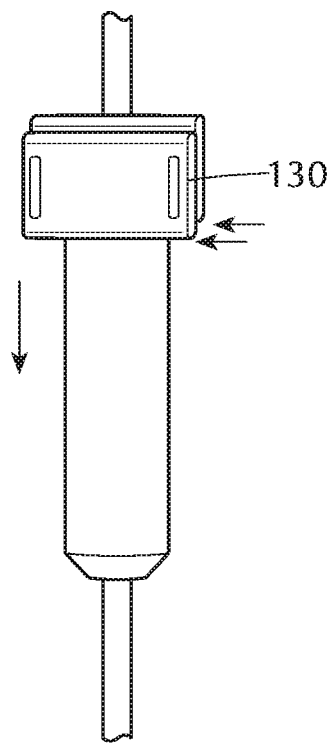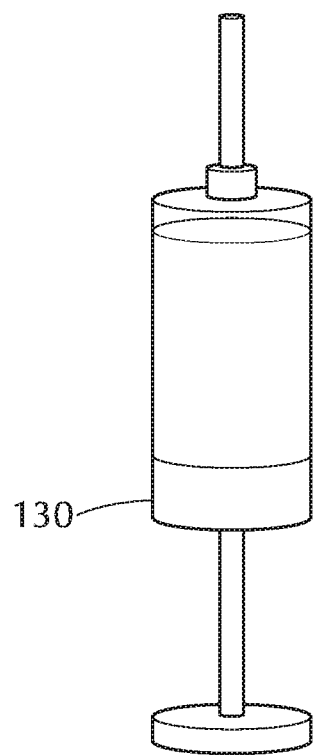
FIG. 4　　　　　　　　FIG. 5
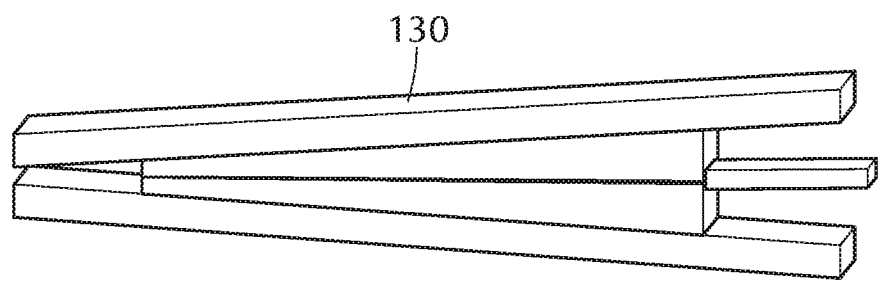
FIG. 6

# INTRAVENOUS TUBING SET MODIFIED FOR IN-LINE CATHETER FLUSHING

CROSS-REFERENCE TO RELATED APPLICATIONS

This application is a continuation of U.S. patent application Ser. No. 14/230,413, filed on Mar. 31, 2014, which claims priority under 35 U.S.C. § 119(e) to U.S. Provisional Application No. 61/807,941, filed Apr. 3, 2013, the disclosures of which are incorporated herein by reference in their entirety.

TECHNICAL FIELD

Aspects of the present invention relate to an intravenous (IV) tubing set which allows for the repeated, sterile flushing of IV catheters using flush solution obtained directly from a source of flush solution, e.g. a saline IV bag.

BACKGROUND

Best clinical practice states that a patient's IV catheter should be routinely flushed with saline to assess catheter function, to clear residual medications, and to lock the catheter during periods of non-use. Where clinical practice dictates bolus flushing, disposable pre-filled syringes are preferred. Elsewhere, saline IV bags are routinely used in clinics for catheter care. The practice of using saline IV bags for catheter maintenance is a "passive" technique, relying only on gravity to deliver the flush solution thru the catheter. To this end, a modified IV tubing set which utilizes IV bag saline would decrease reliance on disposables and make catheter flushing accessible in more clinical settings.

Catheter flushing is an important component of routine catheter maintenance, and infrequent or non-sterile flushes can lead to severe catheter infections (O'Grady, 2011). However, where IV bags are routinely used for catheter care, approaches other than pre-filled syringes may be contemplated.

Therefore, there is a need for an IV tubing set which allows for active flushing procedures by a clinician for the repeated, sterile flushing of IV catheters using saline directly from an IV bag.

SUMMARY

One aspect of the present invention pertains to an intravenous tubing set comprising a coupling component for accessing a source of flush solution; a flush chamber; one or more IV tubing connecting the source of flush solution, the flush chamber and a patient catheter; and one or more flow control devices disposed in the tubing between the source of flush solution and the flush chamber to control the flow of flush solution into the flush chamber. The coupling component may comprise an intravenous bag spike.

In one or more embodiments, the source of flush solution may be an intravenous bag. The flush solution may be a saline solution.

In one or more embodiments, the flush chamber may comprise one or more sheets of flexible plastic film. The one or more sheets of flexible plastic film may be heat-sealed to form the flush chamber. In one or more embodiments, the flush chamber may comprise two heat-sealed sheets of flexible polypropylene.

In one or more embodiments, the flush chamber may be positioned as a bifurcated appendage to the one or more IV tubing or the flush chamber may be positioned in series with the one or more IV tubing. In yet another embodiment, the flush chamber may be disposed partway down the length of the one or more IV tubing to allowing a volume of saline to be measured prior to flushing. The volume of the flush chamber may correlate to a pre-determined flushing volume. In one or more embodiments, the volume of the flush chamber may allow for a 3 mL, 5 mL, or 10 mL flush to be delivered to the patient catheter.

In one or more embodiments, the intravenous tubing set may further comprise an attachment port disposed below the flush chamber. A short length of IV tubing may connect a second source of solution downstream of the flush chamber. The second source of solution may comprise a medication. In one or more embodiments, a second IV tubing may deliver flush solution to a patient catheter from the flush chamber.

In one or more embodiments, the flush chamber allows for tactile feedback to the user during a flush procedure to enable the user to detect the presence of an occlusion in the IV line or in the patient's vein. In one or more embodiments, a bubble trap may also be disposed in the IV tubing.

In one or more embodiments, the flow control device is a valve, clamp, gate, stopcock, diverter or plug. The valve may be a pinch valve or one way valve.

Another aspect of the present invention pertains to an intravenous tubing set comprising a coupling component for accessing a source of flush solution; a flush chamber; a first IV tubing for delivering flush solution from the source of flush solution to the flush chamber; a first flow control device disposed in the tubing between the source of flush solution and the flush chamber to control the flow of flush solution into the flush chamber; a second IV tubing for delivering flush solution to a patient catheter; and a second flow control device disposed in the second tubing between the flush chamber and the patient catheter. The second flow control device may allow for the second IV tubing to be closed as flush solution from the source of flush solution fills the flush chamber. The second flow control device may be subsequently opened to empty the flush solution into the catheter.

In one or more embodiments, the intravenous tubing set may further comprise a third flow control device disposed downstream from the flush chamber to close off the flush chamber during continuous IV therapy.

In one or more embodiments, the flush chamber may be positioned as a bifurcated appendage to the first IV tubing or the flush chamber may be positioned in series with the first IV tubing. In yet another embodiment, the flush chamber may be disposed partway down the length of the first IV tubing to allowing a volume of saline to be measured prior to flushing.

BRIEF DESCRIPTION OF THE DRAWINGS

FIG. 4 shows one embodiment of the present invention having an accessory device comprising rollers.

FIG. 5 shows another embodiment of the present invention having an accessory device comprising a syringe-like device.

FIG. 6 shows yet another embodiment of the present invention having an accessory device comprising hinged plates.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

In this disclosure, a convention is followed wherein the distal end of the device is the end closest to a patient and the proximal end of the device is the end away from the patient and closest to a practitioner.

The present invention relates to an intravenous (IV) tubing set which allows for the repeated, sterile flushing of IV catheters using flush solution directly from a source of flush solution. The embodiments of the present invention provide a low-cost, reusable alternative that integrates catheter flushing into IV tubing sets. By integrating catheter flushing into an IV tubing set, the present invention may reduce the financial barriers that limit catheter flushing in all clinical setting, both in the developing world, as well as, in developed world hospitals.

Figure 1:
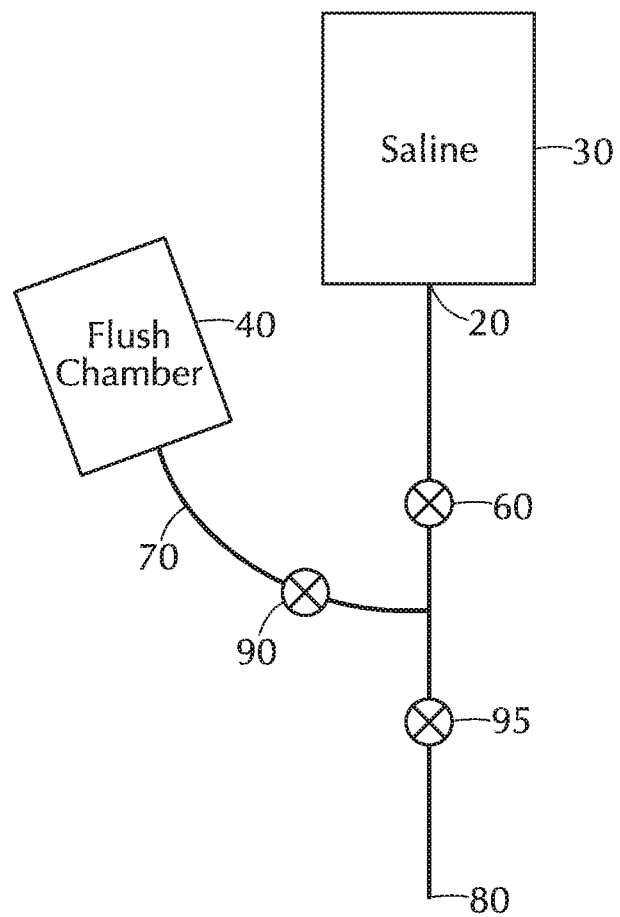
FIG. 1 shows one embodiment of the intravenous (IV) tubing set of the present invention.
Figure 3:
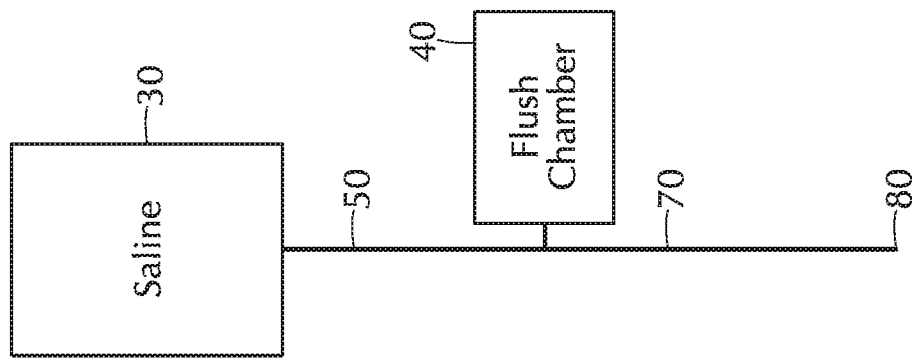
FIG. 3 shows one embodiment of the present invention wherein the flush chamber is positioned as a bifurcated appendage to the IV tubing.
Figure 2:
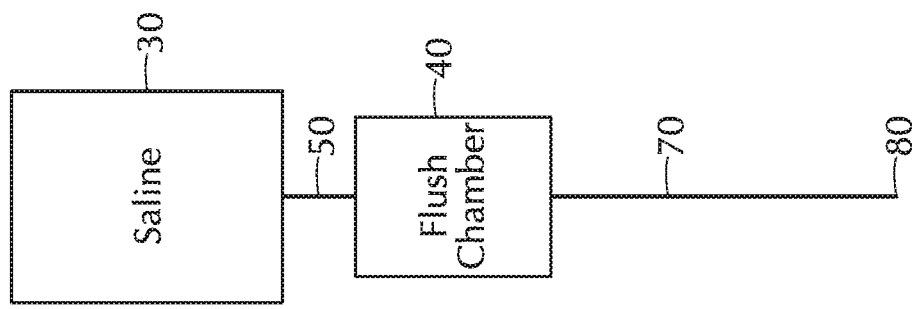
FIG. 2 shows one embodiment of the present invention wherein the flush chamber is positioned in series with the IV tubing.
Figure 7:
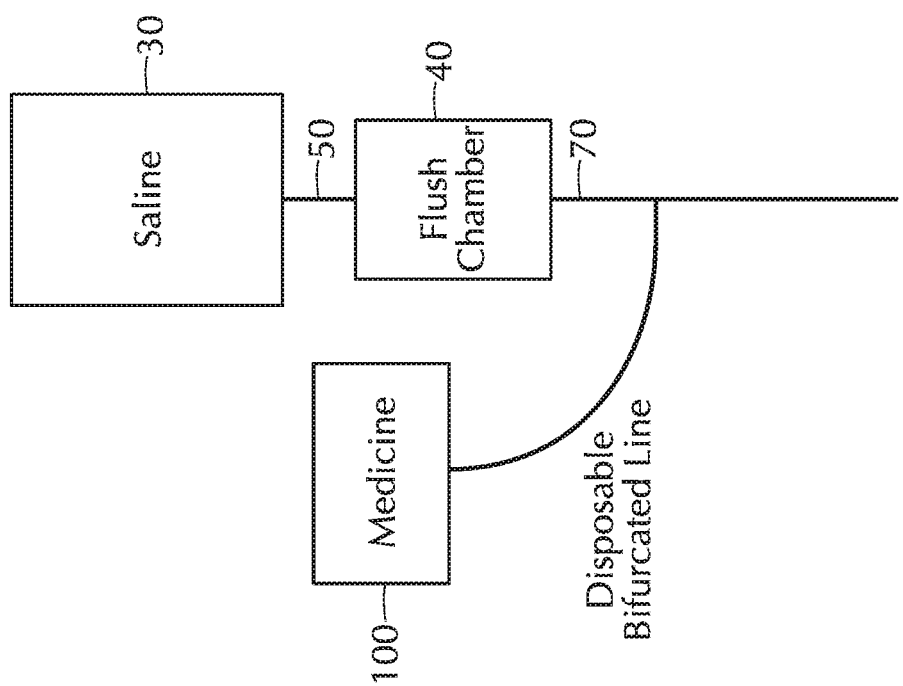
FIG. 7 shows an embodiment of the present invention having a bifurcation for connection to a second source of solution.

As shown in FIG. 1, one embodiment of the present invention provides a closed system intravenous tubing set 10 comprising a coupling component 20 for accessing a source of flush solution 30; a flush chamber 40; a first IV tubing 50 for delivering saline solution from the source of flush solution 30 to the flush chamber 40; a first flow control device 60 disposed in the tubing 50 between the source of flush solution 30 and the flush chamber 40 to control the flow of flush solution into the flush chamber 40; a second IV tubing 70 for delivering flush solution to a patient catheter 80; and a second flow control device 90 disposed in the second tubing 70 between the flush chamber 40 and the patient catheter 80. In one or more embodiments of the present invention, the source of flush solution is an IV bag. In one or more embodiments of the present invention, the flush solution is saline solution. A flexible flush chamber made of polyethylene, polypropylene, other polyolefins, PVC or another material. In one or more embodiments of the present invention, the flexible flush chamber may be located partway down the length of IV tubing, allowing a volume of flush solution to be measured within the tubing system prior to flushing. The volume of the flush chamber may be correlated to a desired flushing volume. Typical flushing volumes are 3 mL, 5 mL, and 10 mL through the catheter. As shown in FIGS. 1 and 3, in one or more embodiments, the flush chamber 40 is a bifurcated appendage to the IV line, which allows a flush solution to be stored within the closed, sterile system between infusions. As shown in FIG. 2, in one or more embodiments, the flush chamber 40 may be positioned in series with the IV tubing for instantaneous flushing. As shown in FIG. 7, in one or more embodiments, an attachment port 100 may be located below the flush chamber 40 for use in settings where it is clinically appropriate to attach a short length of disposable IV tubing to connect an attachment port, such as a medication drip, to a continuous saline flush drip line, thus creating a closed system that includes both medication administration and saline or flush flow.

Flow control devices (60, 90, 95) include, but are not limited to, valves, clamps, gates, stopcocks, diverters and plugs may control the flow of flush solution within the system, between the IV tubing and flush chamber. Valves may include pinch valves or one way valves. In one or more embodiments, a 3-way stopcock or other 3-way junction may also be used as flow control devices to control fluid flow among the source of flush solution, IV tubing, and catheter.

In one or more embodiments, a first flow control device may be positioned between the source of flush solution and the flush chamber to allow for the tubing to be opened as flush solution fills the chamber and then closed as it empties into the catheter. In one or more embodiments, a second flow control device may be positioned between the flush chamber and the catheter to allow for the tubing to be closed as flush solution fills the chamber and then opened as it empties into the catheter. In yet another embodiment, as shown in FIG. 1, if the flush chamber 40 is a bifurcated appendage, a third flow control device 95 is positioned to close off the flush chamber during continuous IV therapy. In the present invention, the flush solution in the source of flush solution, e.g. IV bag, and tubing remains sterile throughout the entire flushing process since the flush chamber and the IV tubing form a closed system. The use of one or more flow control device also ensures sterility because the flow control devices do not come in contact with the fluid.

The flush chamber is flexible to allow for tactile feedback to the user as the flush is performed. Thus, the flush chamber enables the user to detect if there is an occlusion present in the IV line or in the patient's vein.

The IV tubing set of the present invention may be used for the routine flushing of a patient's catheters, both peripheral and central catheters, with flush solution.

Referring to FIG. 1, the use of the IV tubing set of some embodiments is described. First, a first flow control device 60 is opened to allow flush solution to flow from the source of flush solution 30 into the flush chamber 40. Second, the desired volume is measured and the first flow control device 60 is then closed to prevent the flow of additional flush solution into the flush chamber 40. Finally, a second flow control device 90 is opened to allow the flush solution to be manually pushed from the flush chamber 40 into the patient's catheter 80. In one or more embodiments, the user squeezes flush solution out of the flush chamber via use of their hands. As a user pushes the flush solution from the flush chamber 40 into the patient's catheter 80, the user may detect if the line is occluded or if fluid flow is restricted via tactile feedback from the flush chamber. It is important for the user to be able to feel if an occlusion is present in the line so that the catheter does not burst due to increased pressure of continuous medication delivery.

In addition to catheter maintenance, the present invention provides a closed system for the sterile storage and movement of fluid in an IV line. As a result, embodiments of the present invention may be used in several other clinical scenarios where a small amount of sterile liquid is separated from a larger bag attached to an IV line to be delivered through the line.

In one or more embodiments, the size of the flush chamber may be adjusted to accommodate different desired volumes, making the intravenous (IV) tubing set of the present invention adaptable to several clinical needs. Thus, the intravenous (IV) tubing set of the present invention may include a bolus delivery of medication, nutrients, or fluid from a larger IV bag, or the sequestration of one of these liquids from a larger bag for administration separate from the full amount contained in a normally sized IV bag.

An advantage of the invention is that it is a closed, integrated system. By incorporating catheter flushing into an IV tubing set, embodiments of the present invention provide a healthcare worker with all of the supplies required to perform a sterile flush right at the patient's bedside, without any additional supplies, such as a prefilled syringe. Since the integrated IV tubing set of the present invention takes advantage of IV bags and saline IV bags already present in clinical settings, as sources of flush solution, the present invention allows for a decreased reliance on disposables. For example, since many health care providers recommend replacing IV tubing sets every 3-4 days, and up to once per week, it is envisioned that a single IV tubing set of the present invention may be used repeatedly for 3-4 days of flushing or up to a week, thereby eliminating the need for 3-4 days' and up to a week worth of disposable flushing devices.

Embodiments of the present invention also improve upon the sterility of known flushing methods. Specifically, the closed system of the present invention does not expose the inner IV tubing or the patient's catheter to air thereby preserving the sterility of the IV set during each flush. In contrast, the sterility of the IV set during flushes performed using currently known pre-filled devices can be compromised if the user is not thorough in manually sterilizing the patient's catheter with an alcohol swab. The aforementioned scenario is avoided by the present invention which provides a closed system.

Embodiments of the IV tubing set of the present invention also decrease the amount of time required to perform a catheter flush because the clinician does not need to locate any additional materials, such as syringes or alcohol wipes, before performing the flush.

The flush chamber of the present invention may be manufactured by heat sealing two sheets of flexible polyethylene or polypropylene together using a heated metal stamp. The flush chamber may then connected to a main IV tubing line using a second heat seal. Air is subsequently removed from the flush chamber in order to create a vacuum and to prevent air bubbles from being introduced into the patient's IV line during flushing. The IV tubing is threaded through the one or more flow control device before packaging. Other possible manufacturing methods known to a person of skill in the art including producing the flush chamber using adhesive, plastic bonders, heat sealing, or injection molding are also contemplated. In one or more embodiments, the flush chamber may be attached to the IV line using adhesive, plastic bonders or heat sealing to create a completely closed system. In yet another embodiment, the flush chamber and IV line may be manufactured at the same time using heat sealing or injection molding.

In most cases, currently established clinical practice includes preventative air bubble measures thus avoiding improper priming techniques which may allow an air bubble to be introduced into the IV tubing between the flush chamber and the patient's catheter. It is also contemplated that one or more embodiments of the present invention further include a bubble trap that may be added to the IV tubing to prevent an air bubble in the patient's IV tubing.

As shown in FIG. 2, the flush chamber 40 of one or more embodiments of the present invention may be positioned in series with the IV tubing. Positioning the flush chamber in series would allow for flushing boluses within a flush solution line. As shown in FIG. 3, the flush chamber 40 of one or more embodiments of the present invention may also be positioned as a bifurcated appendage to the IV tubing (50, 70). Positioning the flush chamber as an appendage would allow the IV tubing set to function as an uninterrupted line during continuous infusion therapy.

It is contemplated that various devices may be used to assist in dispensing the flush solution from the flush chamber into the patient's catheter. As shown in FIGS. 1-3, the flush chamber may be emptied via manual squeezing without the assistance of an accessory device. However, as shown in FIGS. 4-6, the addition of accessory devices 130 may be used to improve occlusion detection, usability, and volume consistency. Each accessory device, as shown in FIGS. 4-6, may be permanently attached to each IV tubing set or may be shared among multiple sets of IV tubing. FIG. 4 shows one embodiment of an accessory device 130 comprising two rollers that is integrally connected and placed over the flush chamber and may be pressed downward and against one another to empty the flush chamber. The accessory device shown in FIG. 4 may be utilized with an IV tubing set wherein the flush chamber 40 is positioned in series with the IV tubing, as shown in FIG. 2, or with an IV tubing set wherein the flush chamber 40 is positioned as a bifurcated appendage to the IV tubing, as shown FIG. 3. FIG. 5 shows another embodiment of an accessory device comprising a syringe-like push rod device that may be attached to the flush chamber 130. In one or more embodiments, the push rod may also be formed as part of the flush chamber. The accessory devices shown in FIG. 5 may be utilized with an IV tubing set wherein the flush chamber 40 is positioned as a bifurcated appendage to the IV tubing, as shown FIG. 3. FIG. 6 shows yet another embodiment of an accessory device comprising hinged plates that are integrally connected and surround a flush chamber 40 wherein the hinge plates may be used to push against a flush chamber. The accessory device shown in FIG. 6 may be utilized with an IV tubing set wherein the flush chamber 40 is positioned in series with the IV tubing, as shown in FIG. 2, or with an IV tubing set wherein the flush chamber 40 is positioned as a bifurcated appendage to the IV tubing, as shown FIG. 3.

Figure 8:
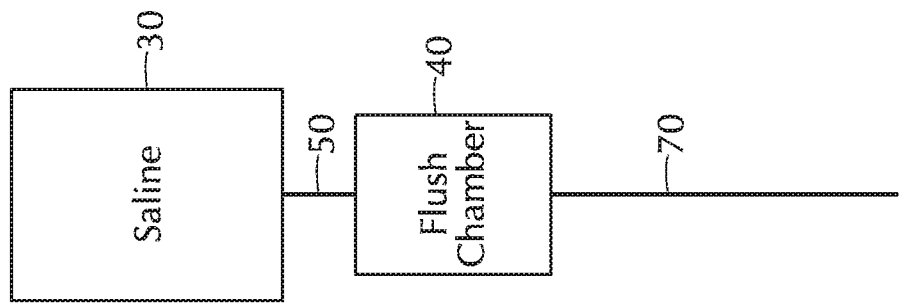
FIG. 8 shows an embodiment of the present invention having a single non-bifurcated line.

As shown in FIG. 7, one or more embodiments of the IV tubing set of the present invention may include a bifurcation for connection to an attachment port 100, e.g. medication bag, allowing a user to perform intermittent saline flushes and medication infusions. Alternatively, as shown in FIG. 8, one or more embodiments of the IV tubing set of the present invention may have a single non-bifurcated line.

Figure 10:
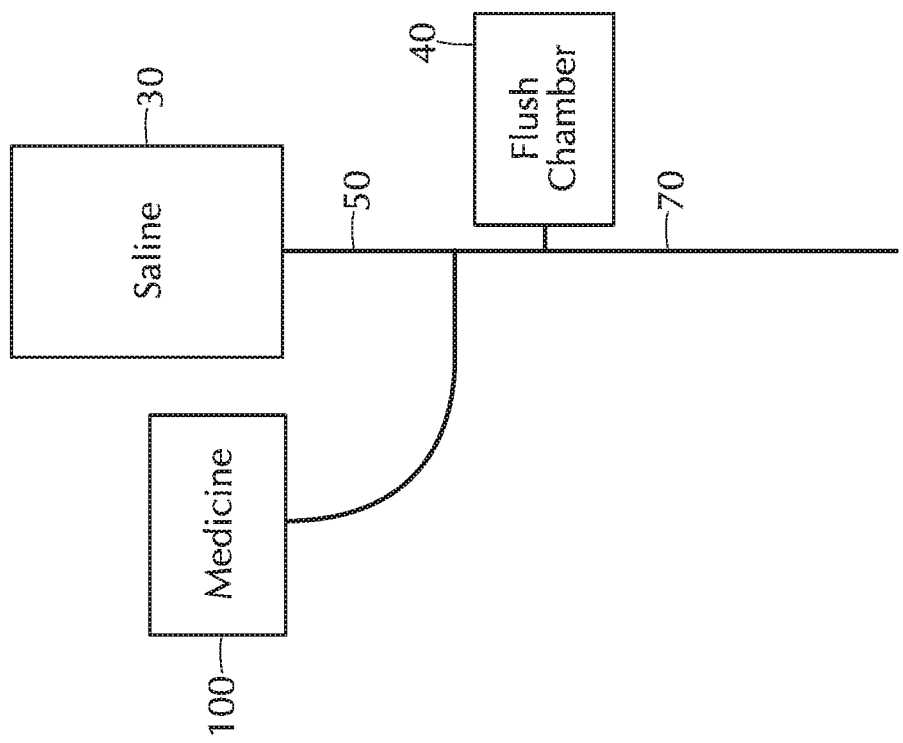
FIG. 10 shows an embodiment of the present invention wherein the flush chamber is disposed further downstream from both the source of flush solution and an attachment port.
Figure 9:
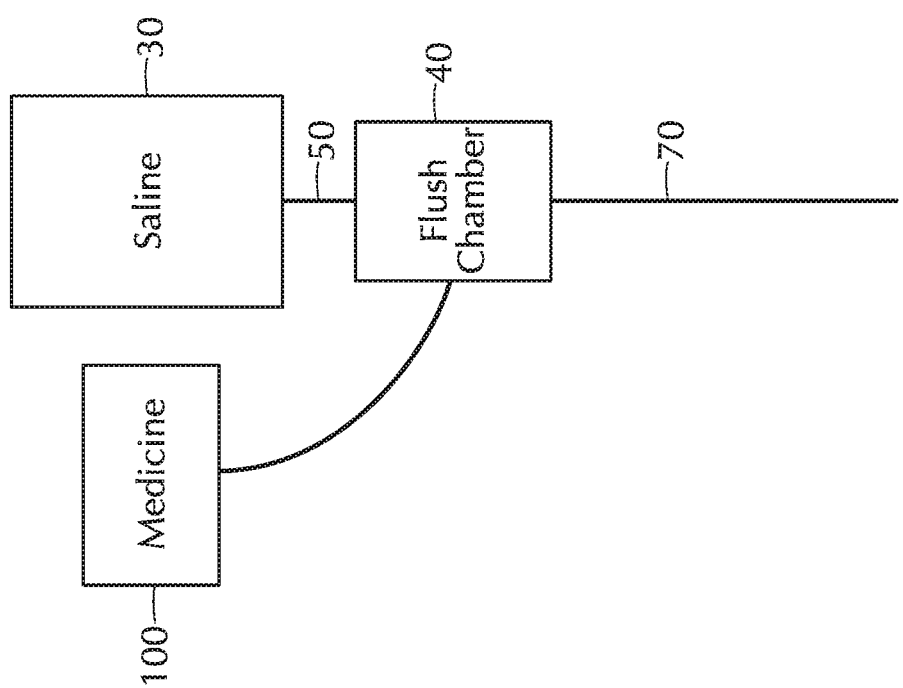
FIG. 9 shows an embodiment of the present invention wherein the flush chamber is disposed immediately downstream from the source of flush solution and upstream from an attachment port.

As shown in FIGS. 9 and 10, the position of the flush chamber 40 may be changed to accommodate other infusion therapy setups. As shown in FIG. 9, the flush chamber 40 may be disposed immediately downstream from the source of flush solution 30 and upstream from the attachment port 100. As shown in FIG. 10, the flush chamber 40 may be disposed further downstream from both the source of flush solution 30, e.g. saline IV bag, and the attachment port 100.

In one or more embodiments, the geometrical shape of the flush chamber may be configured to prevent turbulent flow in the IV line, including but not limited to, cylindrical, trapezoidal bifurcated line and rectangular single line.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A closed intravenous tubing set comprising:
    a coupling component for accessing a source of flush solution;
    a flush chamber having a vacuum, the flush chamber heat-sealed to a first IV tubing connecting the flush chamber and a patient catheter, the flush chamber comprising one or more sheets of flexible plastic film;
    a second IV tubing connecting the source of flush solution and the flush chamber;
    one or more flow control devices disposed in the second IV tubing between the source of flush solution and the flush chamber to control a flow of flush solution into the flush chamber; and
    one or more flow control devices disposed in the first IV tubing between the flush chamber and the patient catheter.

2. The intravenous tubing set of claim 1, wherein the coupling component comprises an intravenous bag spike.

3. The intravenous tubing set of claim 1, wherein the source of flush solution is an intravenous bag.

4. The intravenous tubing set of claim 1, wherein the flush solution is a saline solution.

5. The intravenous tubing set of claim 1, wherein the flush chamber comprises two heat-sealed sheets of flexible polypropylene.

6. The intravenous tubing set of claim 1, wherein the flush chamber is positioned as a bifurcated appendage to the first IV tubing.

7. The intravenous tubing set of claim 1, wherein the flush chamber is positioned in series with the first IV tubing.

8. The intravenous tubing set of claim 1, wherein the flush chamber is disposed partway down a length of the first IV tubing to allowing a volume of saline to be measured prior to flushing.

9. The intravenous tubing set of claim 1, wherein the volume of the flush chamber correlates to a pre-determined flushing volume.

10. The intravenous tubing set of claim 9, wherein the volume of the flush chamber allows for a 3 mL, 5 mL, or 10 mL flush to be delivered to the patient catheter.

11. The intravenous tubing set of claim 1, further comprising an attachment port disposed below the flush chamber.

12. The intravenous tubing set of claim 11, further comprising a short length of IV tubing to connect a second source of solution downstream of the flush chamber.

13. The intravenous tubing set of claim 12, wherein the second source of solution comprises a medication.

14. The intravenous tubing set of claim 1, wherein the flush chamber allows for tactile feedback to a user during a flush procedure to enable the user to detect a presence of an occlusion in the IV line or in a patient's vein.

15. The intravenous tubing set of claim 1, further comprising a bubble trap disposed in the first IV tubing.

16. The intravenous tubing set of claim 1, wherein the flow control device is a valve, clamp, gate, stopcock, diverter or plug.

17. The intravenous tubing set of claim 16, wherein the flow control device is a pinch valve or one way valve.

* * * * *